United States Patent [19]

Murase et al.

[11] Patent Number: 4,785,018

[45] Date of Patent: Nov. 15, 1988

[54] GLYCINE DERIVATIVES

[75] Inventors: Masao Murase, Kusatsu; Shigeaki Maruo, Ibaraki, both of Japan

[73] Assignee: Nippon Shinyaku Co., Ltd., Japan

[21] Appl. No.: 66,820

[22] Filed: Jun. 25, 1987

[30] Foreign Application Priority Data

Jun. 27, 1986 [JP] Japan ................... 61-152149

[51] Int. Cl.⁴ .................. C07C 153/063; A61K 31/24
[52] U.S. Cl. .................................... 514/510; 560/10
[58] Field of Search .......................... 560/10; 514/510

[56] References Cited

U.S. PATENT DOCUMENTS 4,439,617 3/1984 Sestauj ............................ 560/10
4,447,452 5/1984 Sestauj ............................ 560/10
4,568,693 2/1986 Sestauj ............................ 560/10

Primary Examiner—Michael L. Shippen
Attorney, Agent, or Firm—Jacobs & Jacobs

[57] ABSTRACT

A compound of the formula (I):

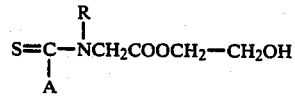

wherein R is hydrogen or unsubstituted or substituted 1-naphthyl. These compounds are useful to obtain inhibition of aldose reductase in animals, including humans.

5 Claims, No Drawings

GLYCINE DERIVATIVES

The present invention relates to glycine derivatives represented by the following general formula (I), which are aldose reductase inhibitors and which are useful in the treatment and/or prevention of diabetic complications:

$$S=\underset{A}{\overset{R}{C}}-NCH_2COOCH_2-CH_2OH \quad (I)$$

wherein R is hydrogen or alkyl having from about 1 to about 4 carbon atoms and A is unsubstituted or substituted 1-naphthyl.

Neuropathy, retinal diseases and renal diseases are three of the main diabetic complications. Neuropathic sequelae are observed in about 50% of diabetic patients within 10 years after the onset of diabetes, while the other two are observed in about 80% of the patients within 20 years.

Aldose reductase is an enzyme that reduces an aldose (such as glucose, galactose, etc.) in humans or other animals to the corresponding polyol (such as sorbitol, galactitol, etc.). Sorbitol, galactitol, etc. produced by this enzyme accumulates in the crystalline lenses, peripheral nerves, kidneys, etc. of patients suffering from diabetes and galactosemia, whereupon the above described diabetic complications are caused. There have been many reports whereby inhibition of aldose reductase has resulted in the prevention or improvement of diabetic complications, including diabetic nervous system disorders, and aldose reductase inhibitors have been proposed for the prevention and/or treatment of diabetic complications.

Compounds (I) of the present invention are aldose reductase inhibitors having excellent pharmacological action with low toxicity.

Japanese published Patent Application No. 57/158,756 discloses Tolrestat, a similar compound to those of the present invention.

The accompanying Examples illustrate representative compounds (I) of the invention. Suitably, the groups R and A may be as exemplified below.

Examples of alkyl having from about 1 to about 4 carbon atoms include straight or branched chain alkyl, such as methyl, ethyl, n-propyl, isopropyl, n-butyl, isobutyl, and the like.

When A is substituted 1-naphthyl there may be one or more, such as 1 to 3, substituents, such as alkoxy of from about 1 to about 4 carbon atoms, halogen and trifluoromethyl.

Examples of alkoxy having from about 1 to about 4 carbon atoms include straight or branched chain alkoxy, such as methoxy, ethoxy, n-propoxy, isopropoxy, n-butoxy, isobutoxy, sec-butoxy, tert-butoxy, etc.

Examples of halogen include chlorine, bromine, iodine, fluorine, etc.

The compounds (I) of the present invention may be manufactured by the following route:

$$S=\underset{A}{\overset{R}{C}}-NCH_2COOR^1 \xrightarrow{HOCH_2-CH_2OH} (I)$$

(II)

wherein R and A are as defined above and $R^1$ is lower alkyl or aryl lower alkyl.

Thus, the ester (II) is reacted with ethyleneglycol by a known method per se to effect transesterification and form (I). The reaction may be carried out using a basic catalyst (e.g. potassium alkoxide, sodium alkoxide, etc.) and when $R^1$ is methyl, a molecular sieve A is preferably present so that the resulting methanol is selectively adsorbed whereupon (I) is prepared in high yield. The reaction temperature may be 50° to 100° C., preferably 60° to 80° C.

Alternatively, an acid catalyst (e.g. sulfuric acid, p-toluene-sulfonic acid, etc.) may be used together with a large excess of ethyleneglycol and when $R^1$ is methyl, the low-boiling methanol is removed whereupon (I) is obtained in high yield.

Alternatively, the free carboxylic acid of (II) may be esterified by known methods to give (I).

Another method for preparing (I) is as follows:

$$A-COOH + R-NHCH_2COOCH_2-CH_2OR^2 \longrightarrow$$
(III) \qquad\qquad (IV)

$$O=\underset{A}{\overset{R}{C}}-NCH_2COOCH_2-CH_2OR^2 \xrightarrow{P_2S_5}$$

(V)

$$S=\underset{A}{\overset{R}{C}}-NCH_2COOCH_2-CH_2OR^2 \longrightarrow (I)$$

(VI)

wherein A and R are as already defined and $R^2$ is a protective group for the hydroxyl group. Any protective group that can be easily removed can be used, such as those usually used as protective groups for hydroxyl groups, such as methyl, trimethylsilyl, tert-butyldimethylsilyl, acetyl, tetrahydropyranyl, methylthiomethyl, methoxymethyl, betamethoxyethoxymethyl, benzyl, and the like.

Each step will be illustrated in more detail as follows.

Compound (III) or a reactive derivative thereof is reacted with (IV) to give (V). This reaction can be carried out by analogy to methods known per se. Suitable reactive derivatives of (III) include, for example, an acid anhydride, acid halide (acid chloride, acid bromide, etc.), activated ester (e.g., imidazolide, 1-benzotriazole, 2,4,5-trichlorophenyl), succinimide, etc.) or a mixed acid anhydride (e.g. anhydride with methyl carbonate; anhydride with ethyl carbonate; anhydride with isobutyl carbonate; etc.).

For example, the activated ester of (III) may be prepared by reacting (III), usually in an inert solvent (e.g. a halogenated hydrocarbon type solvent such as methylene chloride, chloroform, etc; an ether type solvent such as tetrahydrofuran, dioxane, etc.; or an aprotic solvent such as acetonitrile, N,N-dimethylformamide, etc.) with 1-hydroxybenzotriazole or the like and a condensation agent (e.g. N,N'-dicyclohexylcarbodiimide) to convert (III) to the activated ester of (III), which is then condensed with (IV) at −10° C. to room temperature to give (V).

The amount of compound (IV) is preferably 1.2 to 2.5 moles per mole of (III).

The amide ester (V) is then reacted, in an inert solvent (e.g. xylene, toluene, etc.), with phosphorus pentasulfide or Lawesson's reagent under anhydrous condition to give (VI). Preferably, the reaction is conducted in the presence of an organic base, such as N-ethylmorpholine, triethylamine, pyridine, etc.

The reaction temperature is preferably from 80° to 150° C. and, to be more convenient, at the boiling point of the solvent used.

The amount of the phosphorus pentasulfide is preferably 1.1 to 3 moles per mole of (V). The amount of Lawesson's reagent is preferably 0.5 to 2 moles per mole of (V).

The protective group(s) on (VI) is/are removed by conventional methods to give (I).

Compounds (II) and (III) can be manufactured in accordance with a known method (cf. Japanese Published Application No. 57/158756). Compound IV may also be manufactured by known methods.

The resulting compound (I) can be separated/purified by known methods per se, such as, for example, concentration, liquid phase conversion, transferring to another solvent, extraction with solvent, crystallization, recrystallization, fractional distillation, chromatography, etc.

The compounds (I) of the invention are used in the treatment and/or prevention of diabetic complications. In particular, compounds (I) are used to obtain an aldose reductase inhibition effect in animals, including humans, by administering to an animal in need thereof an amount of the compound (I) of the invention effective to inhibit aldose reductase in said animal. Preferably, compound (I) will be administered in the form of a pharmaceutical composition, comprising an effective amount of the compound (I) in combination with a pharmaceutically acceptable, nontoxic, inert diluent or carrier, the carrier comprising one or more solid, semi-solid or liquid diluents, fillers and formulation adjuvants which are nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired aldose reductase inhibition effect upon administration at one application of one or more dosage units according to predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dosage for humans will be from about 1 to about 1000 mg, preferably from about 100 to about 500 mg. In some instances, a sufficient therapeutic effect can be obtained at a lower dose, while in others a large dose will be required.

While the routes of administration of the compound (I) of the invention include oral, parenteral (e.g., intramuscular, intraperitoneal and intravenous), topical and rectal, oral administration is particularly preferred.

The preferred pharmaceutical compositions are therefore those in a form suitable for oral administration, such as tablets, capsules and liquids.

The following Examples are provided for further illustration of the present invention. However, the Examples are not intended the limit the present invention.

EXAMPLE 1 beta-Hydroxyethyl ester of N-[(5-trifluoromethyl-6-methoxy-1-naphthalenyl)thioxomethyl]-N-methylglycine Methyl ester (8.0 g) of N-[{5-(trifluoromethyl)-6-methoxy-1-naphthalenyl}-thioxomethyl]-N-methylglycine suspended in 50 ml of ethyleneglycol was heated with 0.2 g of sodium hydride (60%) at 80° C., stirred for 30 minutes, and stirred for 2 hours more in vacuo. After being cooled, the reaction solution was poured over into ice water weakly acidified with hydrochloric acid, the mixture was extracted with ethyl acetate, the extract was washed with water, dried and concentrated. The resulting residue was purified by a column chromatography (silica gel/chloroform) and the resulting oily substance was crystallised from isopropyl ether followed by recrystallising from chloroform-isopropyl ether to give 4.9 g of pale yellow powder. M.p. 82°–83° C.

Elem. Anal. for $C_{18}H_{18}F_3NO_4S$; Calculated (%) C: 53.86 H: 4.52 N: 3.49. Found (%) C: 54.11 H: 4.64 N: 3.45.

NMR (CDCl$_3$) δ: 2.64 (1H, s, OH, disappeared by D$_2$O), 3.02 (3H, s, N$\underline{CH_3}$), 3.90 (2H, m, —CH$_2$—$\underline{CH_2}$—), 3.98 (3H, s, ArO$\underline{CH_3}$), 4.40 (2H, m, —$\underline{CH_2}$—CH$_2$—), 4.47 (1H, d, J=16 Hz, NC$\underline{H_2}$—), 5.39 (1H, d, J=16 Hz, NC$\underline{H_2}$—), 7.1~7.55 (3H, m, ArH), 8.0~8.4 (2H, m, Ar$\underline{H}$).

IR (KBr) νcm$^{-1}$: 3400, 1750, 1620, 1510, 1390, 1280, 1090.

EXAMPLE 2 beta-Hydroxyethyl ester of N-[(5-iodo-6-methoxy-1-naphthalenyl)thioxomethyl]-N-methylglycine To 20 ml of ethyleneglycol was added 36 mg of 60% sodium hydride and the mixture was stirred at room temperature for 20 minutes. To this was added a solution of 1.95 g of methyl ester of N-[(5-iodo-6-methoxy-1-naphthalenyl)thioxomethyl]-N-methyl glycine in 7 ml of toluene, then 10 ml of ethyleneglycol was added thereto, and the mixture was stirred at 80° C. for 4.5 hours. This was cooled, poured over 10 ml of 0.1N hydrochloric acid which was previously diluted with cold water. The mixture was extracted with ethyl acetate, the extract was washed with an aqueous solution of sodium chloride, dried with magnesium sulphate, filtered, the solvent was evaporated from the filtrate, the residue was subjected to a silica gel column chromatography for separation and purification, isopropyl ether was added thereto to crystallise, and filtered to give 0.98 g of the desired compound. M.p. 115°–119° C.

Elem. Anal. for $C_{17}H_{18}INO_4S$; Calculated (%) C: 44.46 H: 3.95 N: 3.05. Found (%) C: 44.37 H: 3.99 N: 3.10.

$^1H$—NMR(CDCl$_3$) δ: 2.35 (1H, s, OH), 3.00 (3H, s, NCH$_3$), 3.50~4.05 (2H, m, CH$_2$) 3.98 (3H, s, OCH$_3$), 4.25~4.50 (2H, m, CH$_2$) 4.47 (1H, d, J=17.0 Hz, NCH$_2$), 5.36 (1H, d, J=17.0 Hz, NCH$_2$), 7.10~8.21 (5H, m, arom.H).

IR (KBr) νcm$^{-1}$: 3400, 2920, 1750, 1605, 1500, 1450, 1400, 1270, 1190.

TEST EXAMPLES

As hereunder, the result of pharmacological test of the representative compounds of the present invention is given.

TEST METHOD (A) Male rats of Sprague-Dawley strain (body weight: 150 to 200 g) were fasted overnight and used in the test (one group comprised 4 rats). To all groups were given 5 g/kg of galactose orally, then the rats were sacrified after 3 hours, and sciatic nerve was taken out and weighed. The content of galactitol in the sciatic nerve was measured by high performance liquid chromatography in accordance with a method by Jean-Marie Dethy (Anal. Biochem. 143, 119, 1984). The test compound was given orally 4 hours prior to the administration of galactose. To the control group was given 0.5% methylcellulose. The result is given in Table 1.

(B) Non-fasted male rats of Sprague-Dawley strain (5 rats in one group) of 150–220 g body weight were used. To all groups was administered 20% galactose diet (a mixture of galactose and F-2 which is a product of Funahashi Farm) and fed for 4 days. The test compound was given orally at 9 a.m. and 5 p.m. from the first to the fourth day. On the fifth day, the rats were sacrificed, sciatic nerve was taken out, and the amounts of inositol and galactitol in the sciatic nerve were measured by the method as given before. The result is given in Table 2.

It is apparent that the present invention compounds exhibit pharmacological activity out of the Tables 1 and 2.

TABLE 1

| Compound | Inhibition rate (%) against Accumulation of Galactitol in sciatic nerve. The next line shows dose (mg/kg) | |
|---|---|---|
| | 20 | 10 |
| 1 | 92.43 | 62.15 |
| Tolrestat | 28.26 | 21.01 |

TABLE 2

| Compound | Inhibition Rate (%) (The next line is dose) | | |
|---|---|---|---|
| | 5 | 10 | 20 mg/kg |
| 1 | 93 | 95 | |
| Tolrestat | 34 | 86 | 96 |

ACUTE TOXICITY

Male mice of ddY strain (5 weeks of age) were used (one group comprised 4 to 5 mice). The test drug suspended in 0.5% methylcellulose of physical saline was orally given, then usual feeding was done, and the general symptom and the status of death or alive were observed for two weeks. The rate of death is given in Table 3.

TABLE 3

| Compound | 500 | 1000 mg/kg |
|---|---|---|
| 1 | | 0/5 |
| Tolrestat | 2/4 | 3/4 |

Thus, all of the present invention compounds tested had low toxicity and no abnormal change was observed by administration of 1 g/kg.

We claim:

1. A compound of the formula (I):

wherein R is hydrogen or alkyl having from 1 to 4 carbon atoms and A is 1-naphthyl unsubstituted or substituted by one or more alkoxy of 1 to 4 carbon atoms, halogen or trifluoromethyl.

2. The compound according to claim 1, which is beta-hydroxyethyl ester of N-[(5-trifluoromethyl-6-methoxy-1-naphthalenyl)-thioxomethyl]-N-methylglycine.

3. The compound according to claim 1, which is beta-hydroxyethyl ester of N-[(5-iodo-6-methoxy-1-naphthalenyl)thioxomethyl]-N-methylglycine.

4. A pharmaceutical composition for the prevention and/or treatment of diabetic complications in animals, including humans, which comprises an aldose reductase inhibition effective amount of a compound according to claim 1, in combination with a pharmaceutically acceptable carrier or diluent therefor.

5. A method for the prevention and/or treatment of diabetic complications in animals, including humans, which comprises administering to an animal, including humans, in need thereof an aldose reductase inhibition effective amount of a compound according to claim 1.

* * * * *